(12) United States Patent
Robson et al.

(10) Patent No.: US 10,188,554 B2
(45) Date of Patent: Jan. 29, 2019

(54) WOUND DRESSING

(71) Applicant: IWMT Intellectual Property Holdings (Pty) Ltd, Kwa Zulu Natal (ZA)

(72) Inventors: Martin C. Robson, Macatawa, MI (US); Jacobus Frederick Mouton, Centurion (ZA)

(73) Assignee: IWMT Intellectual Property Holdings (Pty) Ltd, Pinetown, Kwa Zulu Natal (ZA)

( * ) Notice: Subject to any disclaimer, the term of this patent is extended or adjusted under 35 U.S.C. 154(b) by 55 days.

(21) Appl. No.: 14/763,754

(22) PCT Filed: Jan. 28, 2014

(86) PCT No.: PCT/IB2014/058599
§ 371 (c)(1),
(2) Date: Jul. 27, 2015

(87) PCT Pub. No.: WO2014/115124
PCT Pub. Date: Jul. 31, 2014

(65) Prior Publication Data
US 2015/0366717 A1 Dec. 24, 2015

(30) Foreign Application Priority Data
Jan. 28, 2013 (ZA) .................................. 2013/00743

(51) Int. Cl.
*A61F 13/00* (2006.01)
*D04H 1/46* (2012.01)

(52) U.S. Cl.
CPC .. *A61F 13/00042* (2013.01); *A61F 13/00029* (2013.01); *A61F 13/00034* (2013.01); *A61F 13/00987* (2013.01); *D04H 1/46* (2013.01); *A61F 13/00991* (2013.01); *A61F 2013/00089* (2013.01)

(58) Field of Classification Search
CPC .......... A61F 13/00029; A61F 13/00034; A61F 13/00042; A61F 13/00063; A61F 13/00987; A61F 13/00991; A61F 13/00995; A61F 2013/00251; A61F 2013/00255; A61F 2013/00323; A61F 2013/51066; A61F 2013/51069
See application file for complete search history.

(56) References Cited

U.S. PATENT DOCUMENTS 3,285,245 A 11/1966 Eldredge et al.
4,984,570 A 1/1991 Langen et al.
(Continued)

FOREIGN PATENT DOCUMENTS

DE 2232820 A1 1/1974
WO 2007046806 A1 4/2007

OTHER PUBLICATIONS

International Search Report of PCT/IB2014/058599 dated May 7, 2014.

*Primary Examiner* — Lynne Anderson
(74) *Attorney, Agent, or Firm* — Amster, Rothstein & Ebenstein LLP

(57) ABSTRACT

The invention relates to a wound dressing for absorbing exudate from a wound on which the wound dressing is placed. The wound dressing includes a porous, highly absorptive fiber dressing and a negative surface charge on a surface of the dressing.

13 Claims, 5 Drawing Sheets

(56) References Cited

U.S. PATENT DOCUMENTS

| | | | | |
|---|---|---|---|---|
| 5,300,192 A | * | 4/1994 | Hansen | A61F 13/0209 156/296 |
| 6,653,520 B1 | * | 11/2003 | Mouton | A61F 13/00008 602/41 |
| 7,112,712 B1 | * | 9/2006 | Ancell | A61F 13/00017 602/41 |
| 7,871,946 B2 | * | 1/2011 | Tsujimoto | D04H 3/12 264/103 |
| 7,955,997 B2 | * | 6/2011 | Messier | A41D 13/1192 424/78.08 |
| 8,088,964 B2 | | 1/2012 | Mouton | |
| 2013/0172843 A1 | * | 7/2013 | Kurata | A61F 13/022 604/372 |

* cited by examiner

WOUND DRESSING

THIS INVENTION relates to wound bed preparation. In particular, the invention relates to a wound dressing.

BACKGROUND OF THE INVENTION

Wound bed preparation is the management of a wound in order to accelerate endogenous healing or to facilitate the effectiveness of other therapeutic measures. To be effective in wound bed preparation a product would have to facilitate debridement of necrotic tissue and debris, decrease excessive wound exudate, decrease the tissue bacterial level, remove deleterious chemical mediators, and set the stage for acceleration of endogenous healing or wound closure by wound approximation, skin graft, or pedicle flap.

The aim of this invention is to provide a wound dressing which can accomplish each of the requirements for effective wound bed preparation.

SUMMARY OF THE INVENTION

According to one aspect of the invention, there is provided a wound dressing, for absorbing exudate from a wound on which the wound dressing is placed, which includes
 a porous, highly absorptive fiber dressing; and
 a negative surface charge on a surface of the dressing.

In use, the wound dressing is placed on a wound. Particularly the wound dressing may be used on a wound that produces excessive exudate.

The wound dressing may include small pores, which act as capillaries. In use, the exudate is attracted to surfaces of the wound dressing, and is attracted into the pores of the wound dressing through capillary action.

The wound dressing may be made of two or more different types of absorbent material.

The absorbent material may have a high hydraulic conductivity, for allowing the liquid exudate to move through the porous dressing as defined by Darcy's Law. The hydraulic conductivity of the absorbent material allows the liquid exudate to move from a higher concentration of liquid (i.e. wetter) to a lower concentration of liquid (i.e. drier) even against gravity. The hydraulic conductivity of the absorbent material further allows liquid exudate to move through the wound dressing both vertically and horizontally.

A first absorbent material may be of non-woven fabric. The non-woven fabric may be composed of any one or more of cotton, viscose and polyester fibers.

A second absorbent material may be in the form of a woven mesh fabric. The woven mesh fabric may be in the form of a woven cotton scrim, woven cotton material or the like.

The first absorbent material and the second absorbent material may be layered onto each other. The first absorbent material and the second absorbent material may be attached to each other.

The wound dressing may include two layers of the first absorbent material, with a single layer of the second absorbent material sandwiched between the two first absorbent material layers. Fibers of the two layers of first absorbent material may protrude through the mesh of the second absorbent material, thereby creating a tri-layer wound dressing having a cross-action structure. The cross-action structure may further assist in the movement of exudate through the wound dressing both vertically and horizontally.

The negative charge may be on a surface of the first absorbent material. Particularly the negative charge may be on a surface of the absorbent material which, in use, is in contact with the wound. The negative charge may be created through friction, corona discharge or the like.

In use, the negative charge on the wound dressing attracts positive ions (cations) from the wound exudate through coloumb forces. The slightly negative charge of the dressing surface together with the cations originating from the wound exudate forms an electric double layer to which the slightly negative charged bacteria, cytokines and the like have an affinity.

The electric double layer may attract negatively charged particles to the surface of the dressing, as the negatively charged particles reach the surface of the dressing, the particles are drawn up through the pores by capillary action and is spread vertically and horizontally through the dressing due to the hydraulic conductivity of the dressing.

The capillary action, electrostatic action and hydraulic conductivity of the dressing in combination, enables the dressing to draw off exudate, debris, bacteria and deleterious cytokines from the wound and into the dressing.

According to a further aspect of the invention, there is provided a method of manufacturing a wound dressing, which includes
 providing two layers of a non-woven fabric composed of any one or more of cotton, viscose and polyester fibers;
 inserting at least one layer of woven cotton scrim between the two layers of non-woven fabric;
 attaching the layers together by needle punching; and
 frictionally creating a negative surface charge on a surface of the wound dressing.

The invention will now be described, by way of example only with reference to the following drawing(s):

DRAWING(S)

In the drawing(s):

EMBODIMENT OF THE INVENTION

Figure 1:
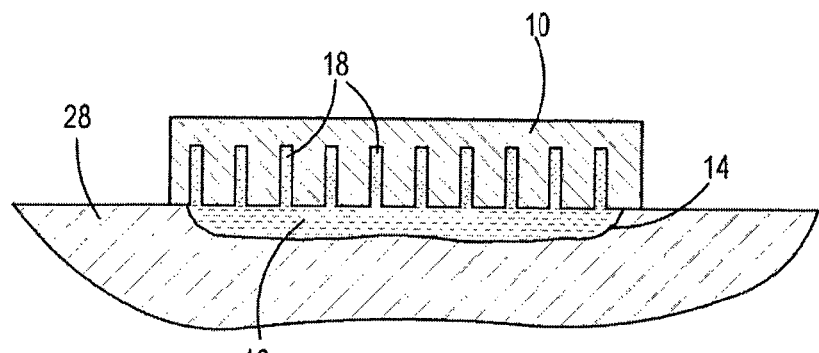
FIG. 1 shows a schematic representation of the capillary action of the wound dressing.
Figure 2:
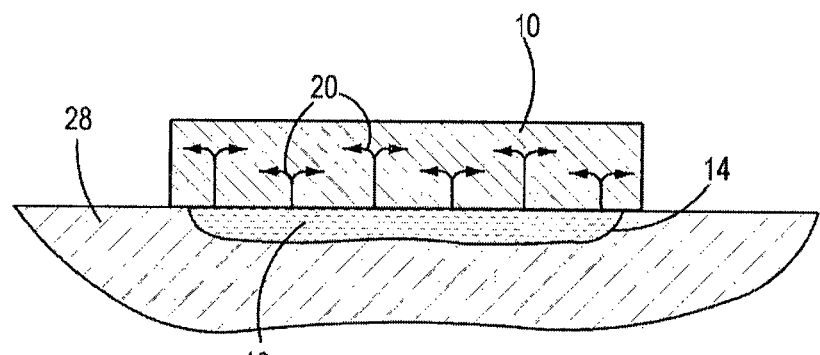
FIG. 2 shows a schematic representation of the effect of the hydraulic conductivity of the wound dressing.
Figure 3:
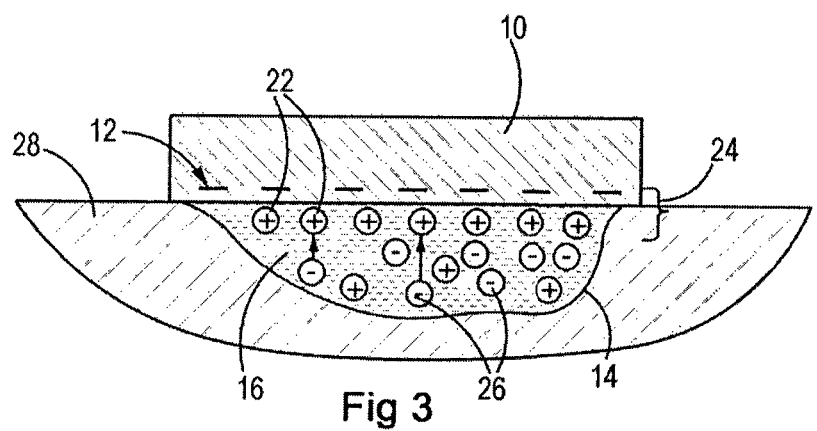
FIG. 3 shows a schematic representation of the electrostatic action of the wound dressing.
Figure 4:
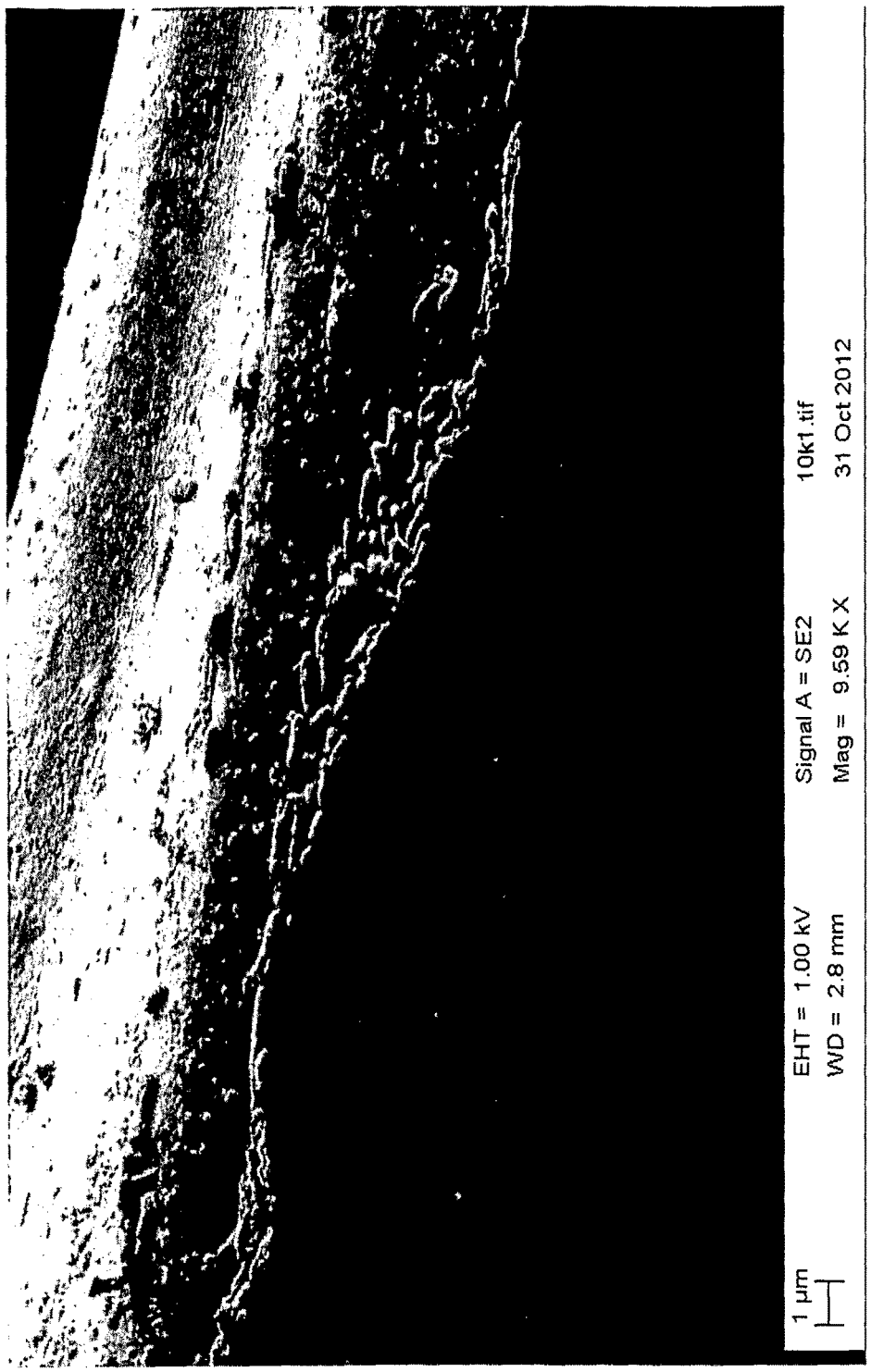
FIG. 4 shows a scanning electron microscopy image of the wound dressing after being immersed in a suspension with *Pseudomonas aeruginosa* overnight.
Figure 5:
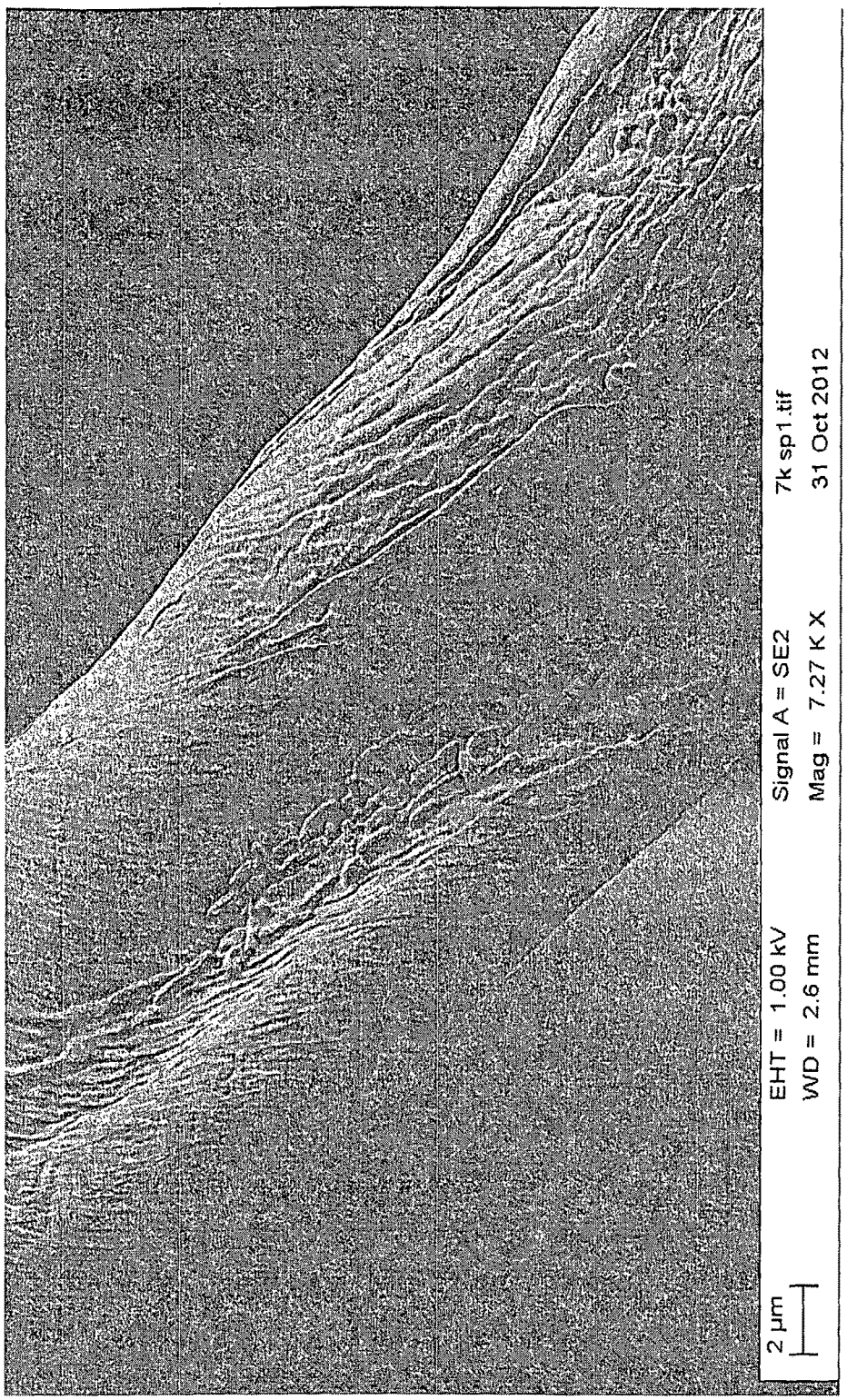
FIG. 5 shows a scanning electron microscopy image of the wound dressing after being immersed in a suspension with *Escherichia coli* overnight.
Figure 6:
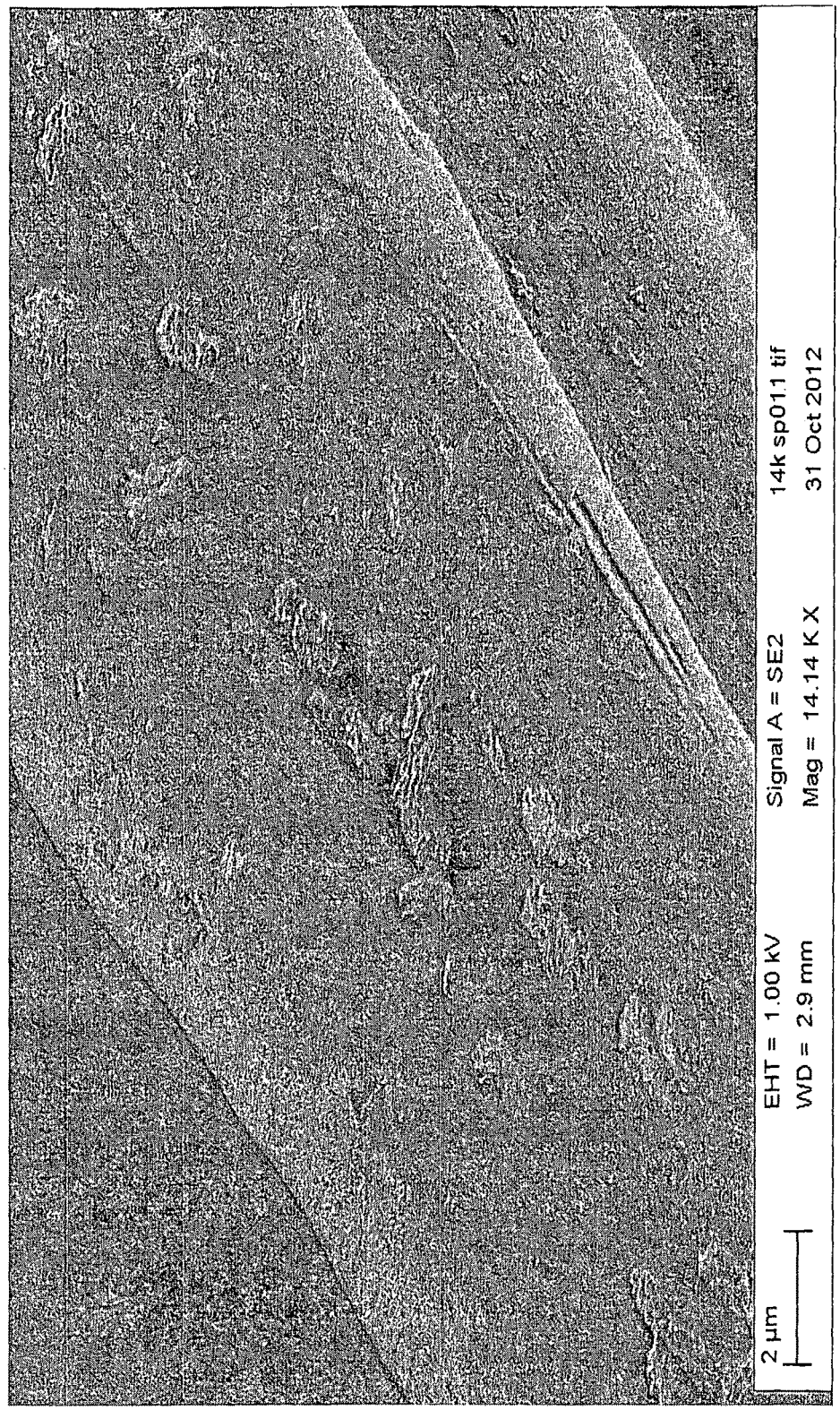
FIG. 6 shows a scanning electron microscopy image of the wound dressing after being immersed in a suspension with *Staphylococcus aureus* overnight.
Figure 7:
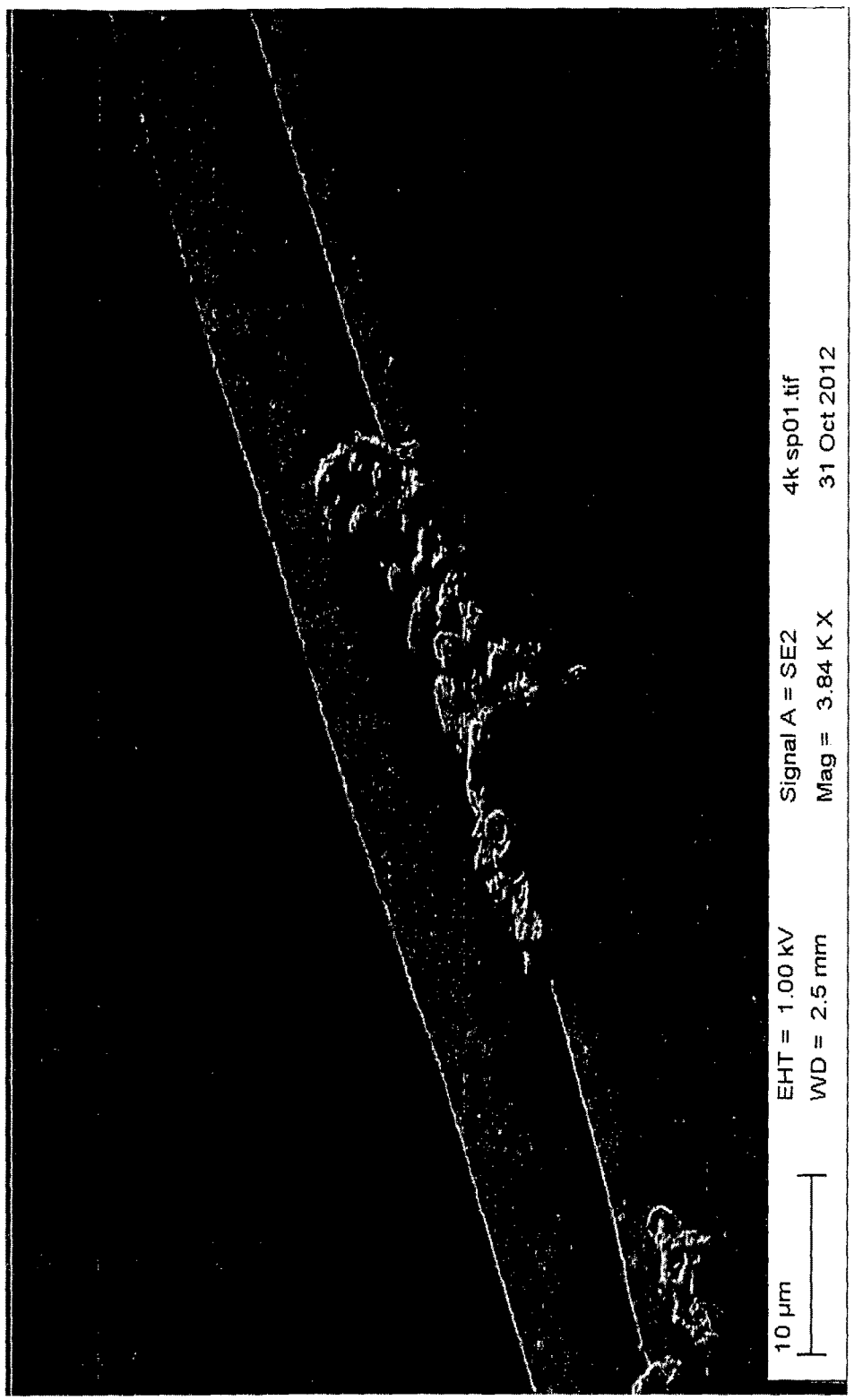
FIG. 7 shows a scanning electron microscopy image of the wound dressing after being immersed in a suspension with *Candida albicans* overnight.

FIGS. 1, 2 and 3 shows schematic representations of the wound dressing in use. Reference numeral 10 refers to a wound dressing in accordance with one aspect of the invention. The wound dressing 10 includes a porous, highly absorptive fiber dressing and a negative surface charge 12 on a surface of the dressing 10.

In use, the wound dressing 10 is placed on a wound 14 on the surface of the skin 28. In this example the wound dressing 10 is specifically used on a wound 14 that produces excessive exudate 16.

As best shown in FIG. 1, the wound dressing 10 includes small pores 18, which act as capillaries. As illustrated, the liquid exudate 16 is attracted to surfaces of the wound dressing 10, and is attracted into the pores 18 of the wound dressing 10 through capillary action.

The capillary action occurs because of inter-molecular attractive forces between the exudate 16 and solid surrounding surfaces of the wound dressing 10. Molecules of water are naturally attracted to each other and form temporary hydrogen bonds with each other, but they are also attracted in a similar way to other molecules, called hydrophilic molecules, such as those in the fibers of the wound dressing 10. These forces can draw liquid upward against the force of gravity to a certain degree. As shown in FIG. 1, the small pores 18 of the wound dressing 10 act as small capillaries, causing it to absorb a relatively large amount of exudate 16.

FIG. 2 shows the effect 20 of the hydraulic conductivity of the wound dressing 10. The wound dressing 10 is made of two different types of absorbent material. The absorbent material has a high hydraulic conductivity, for allowing the liquid exudate 16 to move through the porous dressing 10 as defined by Darcy's Law. The hydraulic conductivity of the absorbent material allows the liquid exudate 16 to move from a higher concentration of liquid (i.e. wetter) to a lower concentration of liquid (i.e. drier) even against gravity. The hydraulic conductivity of the absorbent material further allows liquid exudate 16 to move through the wound dressing both vertically and horizontally.

A first absorbent material is of non-woven fabric. The non-woven fabric is composed of any one or more of cotton, viscose and polyester fibers.

A second absorbent material is in the form of a woven mesh fabric. The woven mesh fabric is in the form of a woven cotton scrim.

The first absorbent material and the second absorbent material are layered on each other and attached to each other. Specifically the wound dressing 10 includes two layers of the first absorbent material, with a single layer of the second absorbent material sandwiched between the two first absorbent material layers. The fibers of the two layers of first absorbent material protrudes through the mesh of the second absorbent material, and creates a tri-layer wound dressing having a cross-action structure. The cross-action structure further assists in the movement of exudate through the wound dressing both vertically and horizontally FIG. 3 shows the electrostatic action between the wound dressing 10 and particles in the wound exudate 16.

The negative charge 12 is on a surface of the absorbent material, which, in use, is in contact with the wound 14. In this example the negative charge 12 is created through friction.

As illustrated in FIG. 3, the negative charge 12 on the wound dressing 10 attracts positive ions (cations) 22 from the wound exudate 16 through coloumb forces. The slightly negative charge 12 of the dressing surface 10 together with the cations 22 originating from the wound exudate 16 forms an electric double layer 24 to which the slightly negative charged particles 26 such as bacteria and cytokines have an affinity.

Electrostatic action is due to the attraction or repulsion between two electrically charged bodies. Bacteria are known to be negatively charged. In Gram-positive bacteria the cell wall has a thick peptoglycan layer which is rich in teichoic acids. These teichoic acids are negatively charged because of the presence of phosphate in their structure. Gram-negative bacteria have an outer membrane composed of phospholipids and lipopolysaccharides. The lipopolysaccharides impart a strongly negative charge to the surface of the Gram-negative bacteria. Matrix metalloproteinases such as MMP-9 are mainly negatively charged soluble proteins, although there can be some variations in electrostatic potentials within the molecules.

When the negatively charged 12 wound dressing 10 surface is in contact with the wound exudate, ions from the exudate form a mobile layer of the opposite charge known as the electric double layer 24 as shown in FIG. 3. These mobile counter ions (cations) 22 are attracted to the negatively charged dressing 10 surface, effectively reversing the charge on the surface of the dressing 10 to become positive, and negating the force of repulsion. The more ions in the exudate, the stronger the electric double layer 24 becomes. Serum and wound exudate contain an abundance of cations which can form the electric double layer.

In addition, there is an attractive force, known as Van der Waals force due to an interaction between oscillating dipoles on surface molecules. Van der Waals force is a very powerful force but only operates over a very small distance. Because the dressing is in intimate contact with the wound exudate, Van der Waals force overcomes any remaining repulsive force.

The electric double layer 24 attracts negatively charged particles 26 to the surface of the dressing 10. As the negatively charged particles 26 reach the surface of the dressing 10, the particles 26 are drawn up through the pores 18 by capillary action and is spread vertically and horizontally through the dressing due to the hydraulic conductivity of the dressing 10.

The effect of the dressing is shown in the scanning electron micrographs in FIGS. 4, 5, 6 and 7. The dressings were immersed in a suspension with *Pseudomonas aeruginosa* (FIG. 4), *Escherichia coli* (FIG. 5), *Staphylococcus aureus* (FIG. 6) and *Candida albicans* (FIG. 7) respectively. The figures shows the interaction of the bacteria and fungi with the dressing, after being immersed in the suspensions overnight. As can be seen in FIGS. 4, 5, 6 and 7 the bacteria and fungi were drawn into the dressing and trapped by fibers in the dressing.

The inventor believes that the invention provides a new wound dressing wherein the capillary action, electrostatic action and hydraulic conductivity of the dressing in combination, improves the ability of the wound dressing to draw off exudate, debris, bacteria and deleterious cytokines from a wound into the dressing.

The invention claimed is:

1. A wound dressing, for absorbing exudate from a wound on which the wound dressing is placed, comprising:
    a porous, highly absorptive fiber dressing made up of two or more different types of absorbent material comprising a first absorbent material in the form of a non-woven fabric and a second absorbent material in the form of a woven mesh fabric; and
    a negative surface charge on a surface of the dressing, wherein the negative surface charge is created though friction, and further wherein the negative surface charge on the wound dressing attracts positive ions from the wound exudate to form an electric double layer that attracts negative charged particles comprising bacteria and cytokines to the surface of the dressing.

2. The wound dressing as claimed in claim 1, in which the wound dressing includes small pores, which act as capillaries, in use, the exudate is attracted to a surface of the wound dressing, and is attracted into the pores of the wound dressing through capillary action.

3. The wound dressing as claimed in claim 1, in which the first absorbent material has high hydraulic conductivity, for allowing the exudate to move through the porous dressing as defined by Darcy's Law, the hydraulic conductivity of the absorbent material allows the liquid exudate to move from a higher concentration of liquid (i.e. wetter) to a lower concentration of liquid (i.e. drier) even against gravity and allows liquid exudate to move through the wound dressing both vertically and horizontally.

4. The wound dressing as claimed in claim 1, in which the non-woven fabric is composed of any one or more of cotton, viscose and polyester fibers.

5. The wound dressing as claimed in claim 1, in which the woven mesh fabric is in the form of any one or more of woven cotton scrim and woven cotton material.

6. The wound dressing as claimed in claim 1 in which the first absorbent material and the second absorbent material are layered onto each other.

7. The wound dressing as claimed in claim 6, in which the first absorbent material and the second absorbent material are attached to each other.

8. The wound dressing as claimed in claim 7, in which the wound dressing includes two layers of the first absorbent material, with a single layer of the second absorbent material sandwiched between the two first absorbent material layers.

9. The wound dressing as claimed in claim 8, in which fibers of the two layers of the first absorbent material protrudes through gaps the mesh of the second absorbent material, thereby creating a tri-layer wound dressing having a cross-action structure, the cross-action structure assisting in the movement of exudate through the wound dressing both vertically and horizontally.

10. The wound dressing as claimed in claim 1, in which the negative charge is on a surface of the first absorbent material.

11. The wound dressing as claimed in claim 1, in which the electric double layer in use, attracts negatively charged particles to the surface of the dressing, as the negatively charged particles reach the surface of the dressing, the particles are drawn up through the pores by capillary action and is spread vertically and horizontally through the dressing due to hydraulic conductivity of the dressing.

12. The wound dressing as claimed in claim 1, in which the wound dressing in use, creates capillary action, electrostatic action and hydraulic conductivity when in contact with wound exudate, enabling the dressing to draw off any one or more of exudate, debris, bacteria and deleterious cytokines from the wound and into the dressing.

13. A method of manufacturing a wound dressing, comprising:
provinding two layers of a non-woven fabric composed of any one or more of cotton, viscose and polyester fibers;
inserting at least one layer of woven cotton scrim between the two layers of non-woven fabric;
attaching the layers together by needle punching; and
frictionally creating a negative surface charge on a surface of the wound dressing so that the wound dressing attracts positive ions from the wound exudate to form an electric double layer that attracts negative charged particles comprising bacteria and cytokines to the surface of the dressing.

* * * * *